United States Patent [19]

Bando et al.

[11] Patent Number: 4,952,409

[45] Date of Patent: Aug. 28, 1990

[54] AGENT FOR PREVENTION AND REMEDY OF INJURIES CAUSED BY ISCHEMIA

[75] Inventors: Ko Bando, Baltimore, Md.; Yoshimasa Senoo, Okayama, Japan; Minoru Noji, Takasaki, Japan; Kazuo Ootsuki, Tokyo, Japan; Hisao Ekimoto, Tokyo, Japan; Yukio Irie, Maebashi, Japan

[73] Assignee: Nippon Kayaku Kabushiki Kaisha, Tokyo, Japan

[21] Appl. No.: 352,752

[22] Filed: May 16, 1989

[30] Foreign Application Priority Data

May 18, 1988 [JP] Japan ............................. 63-119155

[51] Int. Cl.$^5$ .............................................. A61K 37/22
[52] U.S. Cl. ..................................... 424/450; 424/11; 436/829
[58] Field of Search .................. 424/450, 1.1; 264/4.3; 436/829

[56] References Cited

U.S. PATENT DOCUMENTS 4,837,028 6/1989 Allen ................................... 424/450
4,844,904 7/1989 Hamaguchi et al. ................ 424/450

FOREIGN PATENT DOCUMENTS 0200467 12/1987 European Pat. Off. .
61-27901 7/1986 Japan .
61-56201 12/1986 Japan .
62-226928 5/1987 Japan .
18701387 4/1986 PCT Int'l Appl. .

OTHER PUBLICATIONS

J. R. Stewart et al., Ann Thorac. Surg., 42, 390, (1986).
Derwent Accession No. 88-136, 325, Questel Telesystems (WPIL) Derwent Publications LTD., London.
Derwent Accession No. 87-304, 307, Questel Telesystems (WPIL) Derwent Publications LTD., London.

Primary Examiner—Ellis P. Robinson
Assistant Examiner—P. L. Prater
Attorney, Agent, or Firm—Henry C. Nields

[57] ABSTRACT

Disclosed is an agent for prevention and remedy of injuries caused by ischemia, which comprises, as an active ingredient, an SOD-containing liposome comprising a superoxidase dismutase (SOD) retained in a liposome having an electrically neutral or negative membrane.

4 Claims, No Drawings

AGENT FOR PREVENTION AND REMEDY OF INJURIES CAUSED BY ISCHEMIA

BACKGROUND OF THE INVENTION (1) Field of the Invention

The present invention relates to an agent for prevention and remedy of injuries caused by ischemia.

(2) Description of the Related Art

The ischemic disease, a kind of the injury caused by ischemia, is a morbid state caused by bleeding or abnormality of blood properties. As the ischemic disease, there can be mentioned cardiac infarction, cerebral thromobosis, angina pectoris and disseminated intravascular coagulation (DIC) caused by exogenous or endogenous hyperfunction of the coagulating mechanism, which is due to the activation of thromboplastin released from the texture injured by cancer, systemic infection with bacteria or fungi, or hypoxemia. An antithrombotic agent or heparin has been used for the remedy of the ischemic disease, but the effect is yet insufficient. Furthermore, any other agent has not been clinically effectively used for this purpose.

As another injury caused by ischemia, there can be mentioned an injury of an organ for transplantation. Namely, success of transplantation depends greatly on the preservation of the tissue activity at the harvest of the organ, during the storage of the harvested organ and at the transplantation (hereinafter referred to as "preservation").

As the method for the preservation of an harvested organ, which is widely used in the clinical field, there can be mentioned a simple hypothermic immersion preservation and hypothermic perfusion preservation. As the preservation solution generally used, there can be mentioned an electrolyte solution called "intracellular solution" for the simple hypothermic immersion preservation. For example, Collins solution and modified Collins solution are used. For the hypothermic perfusion preservation, a solution prepared by adding electrolytes to plasma components, which is called "extracellular solution", is used. As the means for improving the long-period preservability, there can be mentioned a method in which dimethyl sulfoxide, glycerol or the like is added, as disclosed in Japanese Patent Publication No. 56201/1986, a method in which a protein or glycoprotein modified with a higher alcohol, a fatty acid or an amino acid ester is added, as disclosed in Japanese Patent Application Laid-Open Specification No. 27901/1986, and a method in which a plasminogen activator is incorporated, as disclosed in Japanese Patent Application Laid-Open Specification No. 226928/1987.

As the important cause of the injury to an organ, there can be mentioned generation of active oxygen by ischemia at the harvest of the organ, the preservation of the harvested organ and the transplantation operation, or at the perfusion of an oxygenated preservation solution and reperfusion of blood after the transplantation. Accordingly, there has been tried an organpreserving method in which a superoxide dismutase or catalase is used as oxygen radical scavengers' [see, for example, J. R. Stewart et al., Ann. Thorac. Surg., 42, 390 (1986)].

A freeze preservation method can be considered as the organ preserving method, but this method is not effective because an appropriate agent which prevents freeze injury has not been developed.

In these organ preserving methods, it is only in case of the preservation of the kidney that the improvement of the preservability is attained and there is no appropriate method for the preservation of other organs. Especially in case of preserving, the heart and lung therefore, it is said that the upper limit of the preservation time is 6 hours.

SUMMARY OF THE INVENTION

In accordance with the present invention, there is provided an agent for prevention and remedy of injuries caused by ischemia, which comprises, as an effective ingredient, an SOD-containing liposome comprising a superoxide dismutase (SOD) retained in a liposome having an electrically neutral or negative membrane.

DETAILED DESCRIPTION OF THE INVENTION

Any SOD that can be clinically used can be used in the present invention irrespectively of the kind of the contained metal (any of Cu-Zu type, Fe type and Mn type can be used). For example, SODs derived from erythrocytes, serums, plasmas and SOD-containing organs, such as lung, liver, kidney and placenta, of mammals such as man, bovine, swine, equine, rat and mouse, can be used without any limitation. Moreover, SOD of the Cu-Zn type derived from a vegetable such as spinach and SOD of the Mn type derived from bacteria such as *E. coli* and Serratia can be utilized. SODs produced and purified by the recently developed genetic engineering technique can be used for the agent of the present invention. Among these SODs, there are preferably used SOD of the Cu-Zn type (polymer type secreted intracellularly or extracellularly) having the same amino acid sequence as that of human SOD, and human SOD of the Mn type.

The liposome to be used in the present invention can be prepared according to any known method such as the reverse phase evaporation method or the vortexing method. According to the reverse phase evaporation method, a lipid is dissolved or dispersed in a solvent capable of forming an interface with water, such as ether, chloroform or methylene chloride, an aqueous solution containing an intended substance is added to the solution or dispersion, the mixture is treated by an ultrasonic disperser or emulsifier to form a water-in-oil type emulsion, only the organic solvent is distilled under reduced pressure at 20° to 40° C. to effect gelation, an aqueous phase as the external phase is added to the gel, the mixture is lightly shaken, and the remaining organic solvent is distilled to recover a liposome. According to the vortexing method, a lipid is dissolved in an organic solvent, the solution is charged in an eggplant type flask, the organic solvent is distilled to form a film, an aqueous solution is added, the mixture is heated at a temperature higher than the phase transition temperature of the lipid, and a mechanical vibration is given by a shaker or the like to prepare a liposome.

As the lipid used for the preparation of a liposome having an electrically neutral membrane, there can be mentioned neutral glycerophospholipids such as phosphatidylcholine and phosphatidylethanolamine, sphingolipids such as sphingomyelin and cerebroside, and natural lecithins such as yolk lecithin and soybean lecithin. If an about ($C_{10} \sim C_{20}$) higher fatty acid phosphate ester such as dicetyl phosphate is used in combination with the above-mentioned lipid, a liposome having an electrically negative membrane is obtained. As the lipid to be used for the preparation of a liposome having an electrically negative membrane, there can be mentioned negative glycerophospholipids such as phosphatidylserine, phosphatidylinositol, phosphatidylglycerol, phosphatidic acid and cardiolipin. If the above-mentioned lipid is used in combination with the above-mentioned component forming an electrically neutral membrane and/or the above-mentioned phosphoric acid ester, a liposome having an electrically negative membrane can be obtained. A cholesterol can be used for reinforcing the membrane and α-tocopherol can be used for prevention of oxidation.

When the SOD-containing liposome used in the present invention is prepared, the content of SOD can be changed over a broad range according to the preparation form. The amount of the lipid is 0.05 to 100 parts by weight, preferably 0.5 to 50 parts by weight, per part by weight of SOD, and the aqueous medium is used in an amount of 3 to 1000 parts by weight, preferably 20 to 100 parts by weight, for the phospholipid. Water, a buffer solution, an aqueous solution of sodium chloride and an aqueous solution of a saccharide can be used as the aqueous medium. It is preferred that the pH value of the aqueous solution be adjusted to 5 to 10.

Although the particle size of the SOD-containing liposome is not particularly critical, it is preferred that the average particle size be smaller than 10 μm, especially smaller than about 1 μm. Gel filtration, centrifugal separation or sequential filtration (polycarbonate membrane filtration) can be adopted for uniforming the particle size.

The preparation of the present invention is ordinarily a dispersion in an aqueous medium, but in view of the storage stability, a solid preparation formed by freeze drying, spray drying or the like can be used. Saccharides, amino acids and polymers customarily used in the pharmaceutical field can be used as an excipient for formation of the solid preparation.

The preparation of the present invention is administered to warm-blooded animals such as man, monkey, dog, cat and bovine, for which the prevention and remedy of injuries caused by ischemia are necessary. For example, when the preparation of the present invention is used for prevention and remedy of an ischemic disease such as DIC, the dose differs according to symptoms, body weight, age and the like of an object of administration and clinically the dose is determined by a doctor on duty. In general, the daily dose for an adult is about 25 to about 2500 mg in terms of SOD (about 100,000 to about 10,000,000 U; about 2000 to about 200,000 U per kg of the body weight). In the case where repeated administration is necessary, it is preferred that the daily dose be reduced. Various oral and parenteral administration methods can be adopted, but continuous intravenous infusion is preferred.

In the case where the preparation of the present invention is applied to an harvested organ, the preparation can be administered in the blood vessel of the organ to be transplanted or into a perfusion solution or a preserving solution for the harvested organ at the harvest of the organ and/or at the transplantation of the harvested organ. The dose and the amount of its addition are determined by a doctor on duty. The amount of the preparation administered into the blood vessel and the amount of the preparation added to the perfusion solution at the harvest and/or the transplantation are preferably 5 to 500,000 U/kg in terms of SOD. The amount of the preparation added to the preserving solution for the extracted organ is 20 to 20,000,000 U/l in terms of SOD. More specifically, the amount is controlled to 20 to 2,000,000 U/l in the immersion preservation method and to 200 to 20,000,000 U/l in the perfusion preservation method.

Incidentally, the units of SOD are determined according to the method of Joe M. McCord and Irwin Fridovich [The Journal of Biological Chemistry, Vol. 244, pages 6049–6055 (1969)].

The effect of prevention and remedy of injuries caused by ischemia according to the present invention will now be described with reference to the following experiments.

EXPERIMENT 1

(Samples)

(1) Sample of the present invention; SOD-containing liposome having an electrically neutral membrane; prepared according to the process of Example 1

(2) Sample of the present invention; SOD-containing liposome having an electrically negative membrane; prepared according to the process of Example 2

(3) Control sample; SOD-containing liposome having an electrically positive membrane; prepared according to the process of Referential Example A model of DIC as an example of the ischemic disease was used. Namely, lipopolysaccharide derived from E. coli (LPS, E. coli 055:B5), 100 mg/kg/5 ml, was infused over a period of 4 hours to the left tibiolis anterior vein of a 9-weeks-old female rat (160 to 180 g) of the Wistar Rat under anesthesia with Nembutal. From the point of 30 minutes before the initiation of the administration of LPS, the SOD-containing liposome was infused at a concentration of 66.6 mg (about 250,000 U)/-kg/2 ml over a period of 4.5 hours into the right tibialis anterior vein. Each group consisted of 4 to 6 rates. The preventing effects of the SOD-containing liposome was evaluated based on the measurements of the platelet amount (PLT), the fibrinogen amount (Fbg) and the prothrombin time (PT) in comparison with the group to which the SOD-containing liposome was not administered.

Blood was sampled from the subclavian vein at the start of the experiment and 1, 2, 3 and 4 hours after the start of the experiment. One part by volume of 3.8% sodium citrate was added to nine part by volume of blood to form a sample. PLT was measured by subjecting citrate-containing blood to centrifugal separation to prepare plasma, Fbg was measured by using a fibrinogen test kit (supplied by American Dade American Hospital Supply del Carie, Inc.), and PT was measured by using a prothrombin test kit (supplied by Ortho Diagnostic System Co., Ltd.).

(Results)

The obtained results are shown in Tables 1 through 3.

As is apparent from the results shown in Tables 1 through 3, samples (1) and (2) had effects of preventing and remedying DIC, but control sample (3) did not show such effects.

TABLE 1

| Influences of Samples (1), (2) and (3) on PLT with respect to DIC | | | | | | |
|---|---|---|---|---|---|---|
| | Time (hours) | | | | | |
| Sample | 0 | 1 | 2 | 3 | 4 | Remarks |
| LPS | 100 | 69.6 | 37.4 | 21.0 | 14.4 | control |
| LPS + sample (1) | 100 | 64.9 | 59.3 | 44.6 | 32.6 | present |

TABLE 1-continued

Influences of Samples (1), (2) and (3) on PLT with respect to DIC

| Sample | 0 | 1 | 2 | 3 | 4 | Remarks |
|---|---|---|---|---|---|---|
| LPS + sample (2) | 100 | 72.0 | 56.6 | 44.9 | 33.9 | present invention |
| LPS − sample (3) | 100 | 68.2 | 66.6 | 41.0 | 20.2 | control sample |

Note: the ratio of the value PLT obtained at each time to the value PLT obtained just before administration of LPS (0 hour), which was assumed to be 100%

By the infusion of LPS, the PLT value decreased with the lapse of time.

This decrease was controlled by samples (1) and (2) but was not controlled by control sample (3)

TABLE 2

Influences of Samples (1), (2) and (3) on Fbg with respect to DIC

| Sample | 0 | 1 | 2 | 3 | 4 | Remarks |
|---|---|---|---|---|---|---|
| LPS | 100 | 89.9 | 70.7 | 24.3 | 0.0 | control |
| LPS + sample (1) | 100 | 89.6 | 76.4 | 54.8 | 37.3 | present invention |
| LPS + sample (2) | 100 | 93.9 | 81.9 | 64.7 | 44.3 | present invention |
| LPS + sample (3) | 100 | 87.0 | 76.4 | 50.9 | 0.0 | control sample |

Note: the ratio of the value Fbg obtained at each time to the value Fbg obtained just before administration of LPS (0 hour), which was assumed to be 100%

By the infusion of LPS, the coagulation system exhibited hyperfunction, and the Fbg value decreased with the lapse of time. This decrease was controlled by samples (1) and (2) but was not controlled by control sample.

TABLE 3

Influences of Samples (1), (2) and (3) on PT with respect to DIC

| Sample | 0 | 1 | 2 | 3 | 4 | Remarks |
|---|---|---|---|---|---|---|
| LPS | 100 | 112.0 | 134.7 | 154.8 | 187.7 | control |
| LPS + sample (1) | 100 | 95.4 | 87.7 | 101.1 | 108.4 | present invention |
| LPS + sample (2) | 100 | 115.0 | 110.0 | 134.7 | 147.3 | present invention |
| LPS + sample (3) | 100 | 109.2 | 96.0 | 113.3 | 248.6 | control sample |

Note: the ratio of the value PT obtained at each time to the value PLT obtained just before administration of LPS (0 hour), which was assumed to be 100%

By the infusion of LPS, PT was prolonged. The prolongation was controlled by sample (1) and (2) but not controlled by control sample (3).

EXPERIMENT 2

(Experimental Procedures)

The SOD-containing liposome prepared in Example 6 was used, and mongrel dogs having a body weight of 12.5 to 16.5 kg were used.

Control Group I (seven pairs)

A donor dog was cooled to 15° C. by core-cooling utilizing extracorporeal circulation under general anesthesia, and the heart and lungs were harvested. Just after this harvest, the heart and left lung were excised from a recipient dog and the above-extracted heart and lung of the donor dog were transplanted into the left thorax of the recipient dog.

Control Group II (seven pairs)

A donor dog was cooled to 15° C. by core-cooling utilizing extracorporeal circulation under general anesthesia, and the heart and lung were harvested. The harvested heart was subjected to the retrograde coronary sinus perfusion with an intracellular solution (solution temperature : 4° C., perfusion rate : 30 ml/hr, osmotic pressure : 410 m Osm), and the lung were immersed in an extracellular solution (solution temperature : 4° C., osmotic pressure : 410 m Osm) and stored for 12 hours. The heart and left lung were excised from a recipient dog, and the above-mentioned heart and lung of the donor dog were transplanted in the left thorax of the recipient dog.

Experiment Group I (seven pairs)

The SOD-containing liposome (entrapment:76%) of the present invention was added to the preserving solution used for the above-mentioned Control Group II, that is, at a concentration of 3,000,000 U/l to the intracellular solution and at a concentration of 250,000 U/l to the extracellular solution. Furthermore, the SOD-containing liposome was administered in an amount of 64,800 U/kg of the body weight before the harvest and at the reperfusion after the transplantation.

(Results)

The preservability was evaluated based on the appearance of the lung after the preservation, the compliance of the lung after the transplantation and re-circulation and the pathological observation of the tissue, and the judgement was made in comparison with the Control Group I.

(Appearance of Lung)

| Group | Appearance |
|---|---|
| Control Group I | uniform pink color |
| Control Group II | uneven red color (denser than in Control Group I) |
| Experiment Group I | uniform pink color (almost equivalent to that of Control Group I) |

(Compliance of Lung)

| Group | Compliance |
|---|---|
| Control Group I | good |
| Control Group II | lacking in pliability |
| Experiment Group I | good |

(Pathological Observation of Tissue)

In Control Group I, no thickening of the intima of the blood vessel, and neither hemorrhage nor interstitial edema was found.

In Control Group II, prominent interstitial edema and prominent perivascular hemorrhage were observed, and also focal alveolar wall injury was observed.

In Experiment Group I, no prominent swelling of the epithelium of the alveolus was observed, and though permeation of monocytes in the interstice was observed, neither interstitial edema nor perivascular hemorrhage was observed.

EXPERIMENT 3

Fourteen pairs of calves having a body weight of 30 to 45 kg were used, and after the heart and lung were preserved, the orthotopic transplantation was carried out. The observation was conducted for 6 hours after the transplantation.

A donor calf was cooled to 15° C. under general anesthesia by core-cooling utilizing extracorporeal circulation, and the heart and lungs were harvested. The harvested heart and lungs were preserved for 12 hours in a preserving solution formed by subjecting the blood used for extracorporeal circulation to the anti-coagulating treatment. Then, the preserved heart and lung were transplanted into a recipient calf, from which the heart and lung were similarly excised. Group 1 (six pairs) was a control group, Group 2 (three pairs) was a liposome-free SOD-administered group, and Group 3 (five pairs) was a liposomal SOD-administered group according to the present invention. In Groups 2 and 3, SOD was administered in an amount of 20,000 U/40 kg at the core-cooling. Furthermore, the same amount of SOD was administered either at the transplantation or at the reperfusion after the transplantation. Accordingly, in each of Groups 2 and 3, SOD was contained in the preserving solution.

The effect of the present invention was evaluated and judged by comparing Group 3 with Control Groups 1 and 2 with respect to the survival ratio at the point of 6 hours after the transplantation and the lung function of the living calf.

The lung function was examined with respect to the $PO_2$ (Torr) in blood, indicating the ventilating capacity of the lung, EVLW (extravascular lung water, ml/kg) as the index of the pulmonary edema, the histological score evaluating the lung tissue injury in 6 ranks and the cojugated diene (units) as the index of the amount of the superoxide in the tissue.

The obtained results are shown in Table 4.

TABLE 4

Effects of SOD-Containing Liposome on Extraction, Preservation and Orthotopic Transplantation of Hearts and Lungs in Calves

| | Control Group 1 (untreated group) | | | Control Group 2 (liposome-free SOD-administered group) | | | Group 3 (liposmal SOD-administered group; present invention) | | |
|---|---|---|---|---|---|---|---|---|---|
| Survival ratio | 50% | | | 67% | | | 100% | | |
| Lung function | time (hours) after transplantation | | | | | | | | |
| Analysis Items | 2 | 4 | 6 | 2 | 4 | 6 | 2 | 4 | 6 |
| $PO_2$ (Torr) | 186 | 144 | 102 | 345 | 386 | 302 | 278 | 244 | 187 |
| EVLW (ml/kg) | 11.5 | 11.4 | 13.6 | 7.8 | 8.2 | 6.5 | 9.2 | 10.8 | 10.3 |
| Histol. Score[1] | 4.5 | 4.3 | 4.6 | 2.3 | 2.8 | 3.5 | 2.8 | 3.6 | 4.0 |
| Conjugated diene (unit) | 3.8 | 3.0 | 2.6 | 2.8 | 2.5 | 2.0 | 2.9 | 3.3 | 3.0 |

Note
[1] Histol. Score: histological score

The results shown in Table 4 lead to the following conclusion.

(1) As is apparent from the results of the survival ratio, liposomal SOD has a significant effect of preserving the heart and lung over the control.

(2) In the respective analysis items, liposomal SOD of the present invention is excellent over liposome-free SOD.

(3) Although no prominent difference is found in the data obtained after 2 hours from the transplantation, a significant difference is observed in the lung function as the observation time is prolonged to 4 or 6 hours. In the 12-hour preservation of the heart and lung in which the heart and lung are especially injured, the effect of liposomal SOD of the present invention is confirmed.

(4) Accordingly, liposomal SOD is very suitable for preservation and transplantation of organs.

As is apparent from the foregoing description, the agent of the present invention has a very high effect of preventing and remedying DIC and also is effective in obtaining good results in the transplantation of organs. Therefore, the agent of the present invention is very promising as an agent for prevention and remedy of injuries caused by ischemia.

The process for formation of a preparation containing the agent of the present invention will now be described with reference to the following Examples.

EXAMPLE 1

In 7.5 ml of diethyl ether was dissolved 58.7 mg of dipalmitoylphosphatidylcholine (DPPC) 15.7 mg of dioleylphosphatidylcholine (DOPC) and 9.6 mg of cholesterol (Chol), and 2.5 ml of a phosphate-buffered saline (PBS) solution containing 50 mg/ml (about 200,000 U/ml) of SOD was added to the solution. The mixture was dispersed by a bath-type sonicator and diethyl ether was distilled off in an evaporator to form a gel. Then, 6 ml of PBS was added to the gel and the mixture was dispersed under rotation in the evaporator to obtain a liposome. The liposome was washed by centrifugal separation. The liposomal solution was sterilized by passing the solution through a membrane having a pore size of 0.2 $\mu$m. The obtained liposome was diluted with sterilized PBS to adjust the SOD concentration to 4.8 mg/ml (about 20,000 U/ml) and the dilution was filled in an ampoule to obtain a preparation. The SOD entrapment efficiency was 65%.

EXAMPLE 2

In 7.5 ml of diethyl ether were dissolved 58.7 mg of DPPC, 15.7 mg of DOPC, 9.6 mg of Chol and 5.5 mg of dicetyl phosphate. The solution was treated in the same manner as that described in Example 1 to form a preparation. The SOD concentration was 4.8 mg/ml (about 20,000 U/ml). The SOD entrapment efficiency was 64%.

EXAMPLE 3

In 7.5 ml of diethyl ether were dissolved 78.0 mg of refined yolk lecithin (EPC) and 9.6 mg of Chol, and the solution was treated in the same manner as that described in Example 1. The filled ampoule was freeze-dried to obtain a solid preparation.

EXAMPLE 4

In 7.5 ml of diethyl ether were dissolved 78.0 mg of EPC, 9.6 mg of Chol and 5.5 mg of DCP, and the solution was treated in the same manner as that described in Example 3 to form a solid preparation.

EXAMPLE 5

In 10 ml of chloroform were dissolved 58.7 mg of DPPC, 15.7 mg of DOPC and 9.6 mg of Chol, and chloroform was distilled off under reduced pressure in an evaporator and a desiccator to form a film. Then, 5 ml of a PBS solution containing 50 mg/ml of SOD was added to the film, and heating on a water bath (41° to 50° C.) and vortexing were repeated several times to effect dispersion to thereby obtain a liposome. The liposome was treated in the same manner as that described in Example 1 to obtain a preparation.

The SOD concentration was 4.8 mg/ml (about 20,000 U/ml), and the SOD entrapment efficiency was

EXAMPLE 6

In 75 ml of diethyl ether were dissolved 587 mg of DPPC, 157 mg of DOPC, 55 mg of DCP and 77 mg of Chol, and 25 ml of a PBS solution containing 200,000 U/ml of SOD was added to the solution. The mixture was dispersed by Microfluidizer® (primary pressure:2.3 kg/cm$^2$, secondary pressure:500 kg/cm$^2$, temperature:4° C.). Diethyl ether was distilled off in an evaporator to form a gel. Then, 60 ml of PBS was added to the gel and the mixture was dispersed under rotation in the evaporator to obtain a liposome. The liposome was washed by centrifugal separation and passed through a membrane having a pore size of 0.4 μm. to uniform the particle size (mean particle size: 0.2 μm) and sterilize, whereby 15 ml of a solution containing an SOD-liposome (58,000 U/ml) was obtained. The solution was filled in a vial to obtain a preparation of the agent of the present invention.

EXAMPLE 7

In 75 ml of diethyl ether were dissolved 587 mg of DPPC, 157 mg of DOPC and 77 mg of Chol, and the solution was treated in the same manner as that described in Example 6 to form a preparation.

EXAMPLE 8

In 75 ml of diethyl ether were dissolved 780 mg of refined yolk lecithin and 77 mg of Chol. The solution was treated in the same manner as that described in Example 6. The obtained vial was freeze-dried to obtain a solid preparation.

EXAMPLE 9

In 100 ml of chloroform were dissolved 587 mg of DPPC, 157 mg of DOPC and 77 mg of Chol, and chloroform was distilled off under reduced pressure in an evaporator and a desiccator to form a film. Then 50 ml of a PBS solution containing SOD was added to the film, and heating on a water bath and shaking were repeated several times to effect dispersion to thereby obtain a liposome. Then, the liposome was treated in the same manner as that described in Example 6 to obtain a preparation.

EXAMPLE 10

A preparation was formed in the same manner as that described in Example 6 by using 587 mg of DPPC, 57 mg of DOPC, 28 mg of DCP, 77 mg of Chol and 5 ml of a PBS solution containing 400,000 U/ml of SOD.

REFERENTIAL EXAMPLE

In 7.5 ml of diethyl ether were dissolved 58.7 mg of DPPC, 15.7 mg of DOPC, 9.6 mg of Chol and 2.7 mg of stearylamine (SA), and the solution was treated in the same manner as that described in Example 1 to form a preparation.

The SOD concentration was 4.8 mg/ml (about 200,000 U/ml), and the SOD entrapment efficiency was 62%.

We claim:

1. A method for preventing and remedying injuries of a transplanted organ caused by ischemia, which comprises administering an effective amount of an SOD-containing liposome comprising a superoxide dismutase (SOD) retained in a liposome having an electrically neutral or negative membrane to a warm-blooded animal or an organ of a warm-blooded animal to be transplanted.

2. A method according to claim 1, wherein the SOD is a human SOD.

3. A method according to claim 1, wherein the administration to the organ to be transplanted is effected before the harvest of the organ, during the preservation of the harvest organ, at the transplantation of the organ or at the reperfusion after the transplantation.

4. A method according to claim 3, wherein the preservation of the harvest organ is carried out in an organ preserving solution.

* * * * *